US010449234B2

(12) United States Patent
Chauhan et al.

(10) Patent No.: US 10,449,234 B2
(45) Date of Patent: Oct. 22, 2019

(54) COMPOSITIONS AND METHODS FOR PREVENTION AND TREATMENT OF CORNEAL HAZE AND SCARRING

(71) Applicant: The Schepens Eye Research Institute, Inc., Boston, MA (US)

(72) Inventors: Sunil Chauhan, Cambridge, MA (US); Reza Dana, Newton, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 15/759,203

(22) PCT Filed: Sep. 9, 2016

(86) PCT No.: PCT/US2016/050945
§ 371 (c)(1),
(2) Date: Mar. 9, 2018

(87) PCT Pub. No.: WO2017/044743
PCT Pub. Date: Mar. 16, 2017

(65) Prior Publication Data
US 2018/0256685 A1 Sep. 13, 2018

Related U.S. Application Data

(60) Provisional application No. 62/217,611, filed on Sep. 11, 2015.

(51) Int. Cl.
*A61K 38/18* (2006.01)
*C07K 14/00* (2006.01)
*C07K 14/475* (2006.01)
*A61P 27/02* (2006.01)
*A61K 9/00* (2006.01)

(52) U.S. Cl.
CPC ........ *A61K 38/1833* (2013.01); *A61K 9/0048* (2013.01); *A61P 27/02* (2018.01); *C07K 14/00* (2013.01); *C07K 14/4753* (2013.01)

(58) Field of Classification Search
None
See application file for complete search history.

(56) References Cited

U.S. PATENT DOCUMENTS

| 5,589,451 | A | 12/1996 | Wilson |
| 5,703,047 | A * | 12/1997 | Wilson ............... A61K 38/1833 424/491 |
| 9,556,248 | B2 * | 1/2017 | Cochran ............ C07K 14/4753 |
| 2007/0167935 | A1 | 7/2007 | Serdarevic |
| 2011/0269944 | A1 | 11/2011 | Nakamura et al. |
| 2014/0378391 | A1 | 12/2014 | Horn |

FOREIGN PATENT DOCUMENTS

EP 2025342 A1 2/2009

OTHER PUBLICATIONS

Kojima et al., Cornea, 27(Suppl.1):S25-S30, 2008.*
Sun et al. H-RN, a peptide derived from hepatocyte growth factor, inhibits corneal neovascularization by inducing endothelial apoptosis and arresting the cell cycle. BMC Cell Biol. (Feb. 24, 2013) vol. 14, No. 8, pp. 1-10.
Anitua et al. Plasma rich in growth factors (PRGF-Endoret) stimulates corneal wound healing and reduces haze formation after PRK surgery. Exp Eye Res. Oct. 2013, vol. 115, pp. 153-161.
Jiang et al. HGF suppresses the production of collagen type III and alpha-SMA induced by TGF-beta1 in healing fibroblasts. Eur J Appl Physiol. Jul. 2008, vol. 103, No. 5, pp. 489-493.
Written Opinion from corresponding Patent Appl. No. PCT/US2016/050945, dated Feb. 21, 2017.
International Search Report from corresponding Patent Appl. No. PCT/US2016/050945, dated Feb. 21, 2017.
Calvo, et al., "Comparative in vitro evaluation of several colloidal systems, nanoparticles, nanocapsules, and nanoemuislons, as ocular drug carriers", Journal of Pharmaceutical Sciences, May 1996, 85(5):530-536.
Creighton, et al., "Proteins: Structures and Molecular Properties", Biochemistry and Molecular Biology, Apr. 1985, 13(2):88.
Fantes, et al., "Wound healing after excimer laser keratomileusis (photorefractive keratectomy) in monkeys", Archives of Ophthalmology, 1990, 108(5):665-675.
Gurny, "Ocular therapy with nanoparticles", Polymeric Nanoparticies and Microspheres, 1986, pp. 127-136.
Gurny, "Preliminary study of prolonged acting drug delivery system for the treatment of glaucoma", Pharm Acta Helv., 1981, pp. 130-132.
Kakazu, et al., "HGF Protects Corneal Epithelial Cells from Apoptosis by the Pl-3K/Akt-1./Bad- but not the ERK1/2- mediated Signaling Pathway", Investigative Opthalmology and Visual Science, Oct. 1, 2004, 45(10):3485-3492.
Kreuter, "Nanoparticles", Colloidal Drug Delivery Systems, 1995, Chapter 5, pp. 219-342.
Kompella, et al., "Recent advances in ophthalmic drug delivery", Therapeutic Delivery, Sep. 1, 2010, 1 (3):435-456.
López-Plandolit, et al., "Plasma rich in growth factors as a therapeutic agent for persistent corneal epithelial defects", Cornea, 2010, 29(8):843-848.
McCann, "Advances and Challenges in Topical Ocular Medications", Advanced. Ocular Care, 2011, pp. 23-25.
National Center for Biotechnology Information, "Human hepatocyte growth factor", GenBank Accession No. P14210.2, Jan. 16, 2019, 20 pages.
Zambito, et al., "Polysaccharides as Excipients for Ocular Topical Formulations", Biomaterials Applications for Nanomedicine, Nov. 2011, pp. 253-284.
Zimmer, et al., "Microspheres and nanoparticles used in ocular delivery systems", Advanced Drug Delivery Reviews, Aug. 1995, 16(1):61-73.

* cited by examiner

*Primary Examiner* — Marianne P Allen
(74) *Attorney, Agent, or Firm* — Mintz Levin Cohn Ferris Glovsky and Popeo, P.C.; Ingrid A. Beattie

(57) ABSTRACT

This application discloses ophthalmic formulations and methods for treating and preventing corneal haze and scarring with an hepatocyte growth factor (HGF) agent.

8 Claims, 7 Drawing Sheets

Specification includes a Sequence Listing.

( Blue: DAPI, nuclear stain; Green: CD45, pan-leukocyte marker )

(H&E staining of corneal sections)

SEQUENCE LISTING

```
<160> NUMBER OF SEQ ID NOS: 1

<210> SEQ ID NO 1
<211> LENGTH: 728
<212> TYPE: PRT
<213> ORGANISM: Homo sapiens
```

<400> SEQUENCE: 1

```
Met Trp Val Thr Lys Leu Leu Pro Ala Leu Leu Gln His Val Leu
1               5                  10                  15

Leu His Leu Leu Leu Leu Pro Ile Ala Ile Pro Tyr Ala Glu Gly Gln
         20                  25                  30

Arg Lys Arg Arg Asn Thr Ile His Glu Phe Lys Lys Ser Ala Lys Thr
             35                  40                  45

Thr Leu Ile Lys Ile Asp Pro Ala Leu Lys Ile Lys Thr Lys Lys Val
         50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
             115                 120                 125

Ile Ile Gly Lys Gly Arg Ser Tyr Lys Gly Thr Val Ser Ile Thr Lys
         130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
             180                 185                 190

Asn Pro Glu Val Arg Tyr Glu Val Cys Asp Ile Pro Gln Cys Ser Glu
         195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
             260                 265                 270

Thr Leu Asp Pro His Thr Arg Trp Glu Tyr Cys Ala Ile Lys Thr Cys
         275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
             340                 345                 350

Tyr Cys Arg Asn Pro Asp Gly Ser Glu Ser Pro Trp Cys Phe Thr Thr
         355                 360                 365

Asp Pro Asn Ile Arg Val Gly Tyr Cys Ser Gln Ile Pro Asn Cys Asp
         370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
```

-continued

```
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
            435                 440                 445
Gly Pro Trp Cys Tyr Thr Gly Asn Pro Leu Ile Pro Trp Asp Tyr Cys
            450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
                500                 505                 510
Tyr Arg Asn Lys His Ile Cys Gly Gly Ser Leu Ile Lys Glu Ser Trp
            515                 520                 525
Val Leu Thr Ala Arg Gln Cys Phe Pro Ser Arg Asp Leu Lys Asp Tyr
            530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
            595                 600                 605
Lys Thr Ser Cys Ser Val Tyr Gly Trp Gly Tyr Thr Gly Leu Ile Asn
            610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
                660                 665                 670
Tyr Gly Gly Pro Leu Val Cys Glu Gln His Lys Met Arg Met Val Leu
            675                 680                 685
Gly Val Ile Val Pro Gly Arg Gly Cys Ala Ile Pro Asn Arg Pro Gly
            690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725
```

COMPOSITIONS AND METHODS FOR PREVENTION AND TREATMENT OF CORNEAL HAZE AND SCARRING

CROSS-REFERENCE TO RELATED APPLICATIONS

This application is the U.S. national stage application, filed under 35 U.S.C. § 371, of PCT International Patent Application No. PCT/US2016/050945, filed Sep. 9, 2016, which claims the benefit of and priority under 35 U.S.C. § 119(3) to U.S. Provisional Appl. No. 62/217,611, filed Sep. 11, 2015, the entire contents of each of which are incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under Grant No. W81XWH-11-1-0477 awarded by the Department of Defense. The Government has certain rights in this invention.

FIELD OF THE DISCLOSURE

The present invention relates to compositions and methods for treating and preventing corneal haze and scarring.

INCORPORATION BY REFERENCE OF SEQUENCE LISTING

The contents of the text file named 36770-548001WO_ST25.TXT, which was created on Sep. 7, 2016, and is 6,610 bytes in size, are hereby incorporated by reference in their entireties.

BACKGROUND OF THE DISCLOSURE

Corneal diseases and injuries account for the second leading non-refractive—cause of blindness affecting over 10 million people worldwide. A number of pathological conditions can lead to corneal scarring, including: injuries (e.g. chemical burns/industrial accidents); infection (e.g. contact lens-related infection or optical herpes); and laser vision correction (PRK). Ninety percent of blindness is permanent due to scarring and vascularization. Scarring caused via fibrotic cellular responses, heals the tissue, but fails to restore transparency.

There is a need for prevention or treatment of the significant effects of corneal haze and scarring resulting from disease or injury to prevent visual degradation, including blindness.

SUMMARY OF THE DISCLOSURE

Prior to the compositions and methods described herein, treatments for corneal haze and scarring were often associated with non-selective actions, harmful immunosuppression and/or secondary infection. The invention described herein provides a solution to these and other problems in the field of corneal haze and scarring. The invention described herein also relates to a pharmaceutical formulation for use in the treatment and prevention of corneal haze and scarring resulting from disease or injury. The invention also provides for methods for the treatment and prevention of corneal haze or scarring in a subject in need of such treatment by administering the formulations of the present invention (e.g., topically or subconjunctivally) directly to the eye, e.g., onto the surface of the cornea, or to a region, e.g., region adjacent to the cornea, of the eye of the subject. The subject is preferably a mammal in need of such treatment, e.g., a subject that has been diagnosed with corneal haze or scarring or a predisposition thereto. For example, the subject has suffered one or more injuries (e.g. chemical burns/industrial accidents), infection (e.g. contact lens-related infection or optical herpes), and/or laser vision correction (PRK) surgery or is expected to undergo a surgery. The mammal can be any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Corneal haze or scarring is a clouding or reduction in transparency of the cornea. It can be a side effect of ocular disease, injury or surgery, e.g., as a result of an agressive wound response. Corneal haze or scarring describes a cloudy or opaque appearance of the cornea. The cornea is normally clear, so corneal haze can greatly impair vision. Although the haze or scarring can occur in any part of the cornea, it is most often found within the thicker, middle layer of the cornea, called the stroma. Corneal haze or scarring is most often caused by inflammatory cells and other debris that is activated during trauma, infection or surgery. Corneal haze or scarring can be graded on a scale of 1 to 4 as shown in Table 1 below. Accordingly, in embodiments, identifying a subject in need of treatment comprises determining or calculating the grade scale (e.g., trace, mild, moderate, or severe) of the subject's cornea transparency.

TABLE 1

Grading Scale for Corneal Haze/Scarring

| | | |
|---|---|---|
| None | 0 | Transparent, clear |
| Trace | +1 | Minimal loss of transparency. Only the epithelium and/or the anterior half of the stroma is involved as observed with an optical section of the slit lamp. |
| Mild | +2 | Dull-glass appearance. The cloudiness extends past the anterior half of the stroma. |
| Moderate | +3 | Involvement of the entire thickness of the stroma. The affected stroma has lost its marble-like appearance and is homogeneously white. With optical section, the endothelium is still visible. |
| Severe | +4 | Involvement of the entire thickness of the stroma. With optical section, cannot clearly visualize the endothelium. |

A method of treating corneal haze or scarring is carried out by identifying a subject who has been identified as having experienced an incident or predilection to corneal haze or scarring, and administering to an ocular or adnexal tissue a composition comprising an effective amount of a purified hepatocyte growth factor (HGF) agent or compound that binds to and/or induces HGF or cMET mediated signal transduction. In the present context an HGF agent may include HGF, or a truncation, modification, mimetic, agonist or analog thereof. An HGF agent is able to induce HGF-mediated signal transduction by HGF-receptor (HGFR or cMET), and may include, without limitation, a natural protein, recombinant protein or peptide and fusion or chimeric protein able to bind HGFR, and biologic or chemical small molecule agonist of HGFR. A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons. HGF agents can be used alone or in conjunction with additional HGF agents or other therapies. However, HGF agents are not inclusive of other growth factors including epidermal growth factor (EGF), fibroblast growth factor (FGF), platelet-derived growth factor (PDGF), nerve growth factor (NGF) and synthetic or naturally occurring mixtures thereof including plasma rich in growth factors (PRGF).

The pharmaceutical formulations of the present invention (e.g., HGF agents) are formulated for ophthalmic delivery, e.g., corneal delivery or administration such that the corneal stroma is permeated. Stromal cells are physiologically and phenotypically different from epithelial cells and it is in the stroma, not any other layer of the cornea, where haze and scarring is seen. For example, the pharmaceutical compositions are formulated for subconjunctival administration. In embodiments, the administration includes contacting the compositions described herein with corneal stroma or corneal stromal cells in a subject in need thereof. Alternatively, the pharmaceutical compositions are formulated for topical administration to the eye or region of the eye. For example, the formulation may comprise one or more tear substitutes. The formulation alternatively comprises an ophthalmic lubricant.

The pH of the formulation is between 5.5 and 7.5 (e.g., about 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5). For example, the pH of the formulation is about 7.4. The formulation is in the form of a single dose unit or in the form of a multi-dose system.

Suitable forms of the composition include a solid, a paste, an ointment, a gel, a liquid, an aerosol, a mist, a polymer, a film, an emulsion, or a suspension. In some cases, the composition is incorporated into or coated onto a contact lens. Preferably, the formulation is an aqueous formulation. The term "aqueous" typically denotes an aqueous composition wherein the carrier is to an extent of >50%, more preferably >75% and in particular >90% by weight water.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Similarly, cell populations are substantially free of other cellular material, or culture medium. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

In some cases, the method further comprises the administration of a second therapeutic agent. For example, a second therapeutic agent includes a steroid, other biologic or small molecule-based anti-inflammatory treatments (e.g. cytokine targeting).

The HGF agent is administered at a frequency that affords optimal effectiveness. For example, the HGF agent is administered every 72 hours, every 48 hours, every 24 hours, every 12 hours, every 6 hours, every 3 hours, every 1 hour, or any other appropriate interval. The HGF agent is administered for 1 day, 2 days, 3 days, 4 days, 5 days, 7 days, 14 days, 30 days, 60 days, 90 days, or 120 days. Administration may be following an injury or insult to the corneal, or administered prior to surgery to prevent corneal haze and scarring from occurring. Injury or insult to the cornea may be the result of injuries (e.g. chemical burns/industrial accidents); infection (e.g. contact lens-related infection or optical herpes); and laser vision correction (PRK). Alternatively, the HGF agent is administered for long-term use, i.e., more than 120 days, more than 150 days, more than 180 days, more than 210 days, more than 240 days, more than 270 days, more than 300 days, more than 330 days or more than 360 days.

Also provided is a method of preventing corneal haze or scarring comprising identifying a subject who is at risk for developing corneal haze or scarring, and administering to an ocular or adnexal tissue a composition comprising an effective amount of an HGF agent. In some cases, the subject is asymptomatic, but at high risk for developing corneal haze or scarring.

Optionally, the method further comprises the administration of a pharmaceutically acceptable carrier. The phrase "pharmaceutically acceptable" is art-recognized and refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The method may further comprise administration of an "ophthalmically acceptable" carrier.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Optionally, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) liposome-based excipients; (22) cyclodextrin; (23) nanoparticle-based excipients and (24) other non-toxic compatible substances employed in pharmaceutical formulations.

Excipients for topical administration of the compositions of the present invention preferentially promote drug penetration through the ocular surface and corneal epithelium and into the corneal stroma. Example excipients that are suitable for preferential drug delivery, e.g., at least 10%, 25%, 50%, 75%, 2-fold, 5-fold, 10-fold, or more, to the corneal stroma compared to other ocular anatomical locations include polysaccharides and derivatives thereof (e.g., chitosan, n-carboxymethyl chitosan, chitosan HCL, N-trimethylchitosan, xyloglucan, hyaluronic acid, alginic acid, cellan gum, cyclodextrans, etc.); nanoparticles (e.g., nanoparticles conjugated, e.g., covalently linked, to a drug of the present invention); liposomes, e.g., into which or onto which the compound/therapeutic agent is associated or linked; surfactants; benzalkonium chloride; and EDTA. A liposome is spherical vessel having at least one lipid bilayer. A nanoparticle is a microscopic particle with at least one dimension less than 100 nm. These excipients may be used as a single excipient or in combinations.

The phrase "ophthalmically acceptable" refers to compositions comprising excipients, emulsifiers, wetting agents, carriers or fillers that are suitable for application to the tissues of the eye and eye area. Such ophthalmically acceptable compositions may comprise for example, the polyethylene glycols designated 200, 300, 400 and 600, or Carbowax designated 1000, 1500, 4000, 6000 and 10000, complexing agents, such as disodium-EDTA or EDTA, antioxidants, such as ascorbic acid, acetylcysteine, cysteine, sodium hydrogen sulfite, butyl-hydroxyanisole, butyl-hydroxy-toluene; stabilizers, such as thiourea, thiosorbitol, sodium dioctyl sulfosuccinate or monothioglycerol; or other excipients, such as, for example, lauric acid sorbitol ester, triethanol amine oleate or palmitic acid ester.

Other carriers and excipients are known in the art, for example those described in: Kreuter, J. "Nanoparticles" *Colloidal Drug Delivery Systems*, edited by Jork Kreuter, Marcel Dekker. New York, N.Y. (USA), chapter 5, page 219 (1994); Gurny, R. "Ocular therapy with nanoparticles" *Polymeric Nanoparticles and Microspheres* edited by P. Guiot and P. Couvreur. Boca Raton, Fla. (USA): CRC Press, page 127 (1986): Gurny, R. "Preliminary study of prolonged acting drug delivery system for the treatment of glaucoma" *Pharm Acta Helv.*, volume 56, page 130 (1981); Zimmer, et al. "J. Microspheres and nanoparticles used in ocular delivery systems" *Advanced Drug Delivery Reviews*, volume 16, number 1, pages 61-73 (1995); Zambito, et al. "Polysaccharides as excipients for Ocular Topical Formulations" *Biomaterials Applications for Nanomedicine*, Prof. Rosario Pignatello (Ed.), ISBN: 978-953-307-661-4, InTech, Available from: http://www.intechopen.com/books/biomaterials-applications-for-nanomedicine/polysaccharidesas-excipients-for-ocular-topical-formulations at pages 253-284; Kompella, et al. "Recent Advances in Ophthalmic Drug Delivery" *Ther Deliv.* 2010 Sep. 1, 1(3): 435-456; McCann, J., "Advances and Challenges in Topical Ocular Medications" *Advanced Ocular Care*, March 2011, at pages 23-25; and Calvo, et al. "Comparative in vitro evaluation of several colloidal systems, nanoparticles, nanocapsules, and nanoemulsions, as ocular drug carriers" *J Pharm Sci*, volume 85, number 5. pages 530-536 (May 1996). These references are incorporated in their entirety by reference herein.

As used herein, the term "tear substitute" refers to molecules or compositions which lubricate, "wet," approximate the consistency of endogenous tears, aid in natural tear build-up, or otherwise provide temporary relief of dry eye symptoms and conditions upon ocular administration.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99-100%, by weight, free from the proteins and naturally-occurring organic molecules with they are naturally associated.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques.

Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) Proteins, W.H. Freeman and Company, incorporated herein by reference. Table 2 below provides example amino acid substitutions.

TABLE 2

Conservative Amino Acid Substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |

TABLE 2-continued

Conservative Amino Acid Substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide.

The term "percent sequence identity" or "percentage sequence identity" refers to the overlap of sequences in an amino acid or nucleic acid sequence. As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (available at the world wide web site ("www") of the National Center for Biotechnology Information (".ncbi") of the National Institutes of Health (".nih") of the U.S. government (".gov"), in the "Blast" directory ("/BLAST/"). The default parameters for comparing two sequences (e.g., "Blast"-ing two sequences against each other), by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=11, and extension gap=1. Additional, computer programs for determining identity are known in the art.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection.

HGF agents of the present invention may include a polypeptide having an amino acid sequence that is at least 50%, at least 60%, at least 70%, at least 80%, at least 85%, at least 90%, at least 95%, at least 96%, at least 97%, at least 98%, at least 99%, at least 99.5%, or at least 99.9% identical to human HGF (SEQ ID NO: 1).

Although the phrase "nucleic acid molecule" primarily refers to the physical nucleic acid and the phrase "nucleic acid sequence" refers to the linear list of nucleotides of the nucleic acid molecule, the two phrases can be used interchangeably.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to reduce or prevent corneal haze or scarring disease in a mammal. In some cases, an effective amount is an amount sufficient to inhibit differentiation of corneal fibroblasts upon treatment with a composition described herein for at least about 10%, 20%, 30%, 40%, 50%, 60%, 70%, 80%, 90% or more compared to the level without treatment of a composition described herein. In some cases, an effective amount is an amount sufficient to inhibit α-smooth muscle actin (αSMA) expression upon treatment with a composition described herein for at least about 10%, 20%, 30%, 40%, 50%, 60%, 70%, 80%, 90% or more compared to the level without treatment of a composition described herein. In some cases, an effective amount is an amount sufficient to increase stratification of corneal epithelial cells upon treatment with a composition described herein for at least 10%, 20%, 30%, 40%, 50%, 60%, 70%, 80%, 90% or more compared to the level without treatment of a composition described herein. In some cases, an effective amount is an amount sufficient to increase c-met expression upon treatment with a composition described herein for at least 10%, 20%, 30%, 40%, 50%, 60%, 70%, 80%, 90% or more compared to the level without treatment of a composition described herein. In some cases, an effective amount is an amount sufficient to restore the thickness of an injured cornea to about 50%, 60%, 70%, 80%, 90%, 95% or higher percentage of the normal (i.e., healthy) cornea thickness. Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, e.g., corneal haze or scarring, so as to effect a reduction in severity and/or frequency of symptoms, eliminate the symptoms and/or their underlying cause, and/or facilitate improvement or remediation of damage.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause, e.g. being characterized as a PRK patient, chemical burn victim, or ocular injury victim.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Human hepatocyte growth factor (GenBank Accession No.: P14210.2) has the following amino acid sequence (SEQ ID NO: 1):

interest can be made by either recombinant, synthetic, or proteolytic digestive methods. Such fragments can then be isolated and tested for their ability to co-stimulate T cells by procedures described herein.

For example, the mature protein comprises amino acid 32-494 (underlined). Other examples include, amino acids 126-207, 208-289, 302-384, and 388-470 each of which comprise Kringle domains which may each, individually be involved in binding mediators.

Accordingly, the HGF agents described herein may include a polypeptide having an amino acid sequence of SEQ ID NO: 1. In embodiments, the HGF agents described herein may include a polypeptide having an amino acid sequence of residues 32-494 of SEQ ID NO: 1. In embodiments, the HGF agents described herein may include a polypeptide having an amino acid sequence of residues 126-207 of SEQ ID NO: 1. In embodiments, the HGF agents described herein may include a polypeptide having an amino acid sequence of residues 208-289 of SEQ ID NO: 1. In embodiments, the HGF agents described herein may include a polypeptide having an amino acid sequence of residues 302-384 of SEQ ID NO: 1. In embodiments, the HGF agents described herein may include a polypeptide having an amino acid sequence of residues 388-470 of SEQ ID NO: 1.

The HGF agents described herein may include a fragment of SEQ ID NO: 1. A fragment can be between 3-10 amino acids, 10-20 amino acids, 20-40 amino acids, 40-56 amino acids in length or even longer. Amino acid sequences having

```
  1  mwvtkllpal llqhvllhll llpiaipyae gqrkrrntih efkksakttl ikidpalkik 61  tkkvntadqc anrctrnkql pftckafvfd karkqclwfp fnsmssqvkk efghefdlye 121  nkdyirncii gkgrsykgtv sitksgikcq pwssmipheh sflpssyrqk dlqenycrnp 181  rqeeggpwcf tsnpevryev cdipqcseve cmtcngesyr qlmdhtesqk icqrwdhqtp 241  hrhkflpery pdkgfddnyc rnpdgqprpw cytldphtrw eycaiktcad ntmndtdvpl 301  etteciqggg eqyrgtvnti wngipcqrwd sqyphehdmt penfkckdlr enycrnpdgs 361  espwcfttdp nirvgycsqi pncdmshgqd cyrgngknym gnlsqtrsgl tcsmwdknme 421  dlhrhifwep dasklnenyc rnpdddahgp wcytgnplip wdycpisrce qdttptivnl 481  dhpviscakt kqlrvvngip trtnigwmvs lryrnkhicg gslikeswvl tarqcfpsrd 541  lkdyeawlgi hdvhgrgdek ckqvlnvsql vygpegsdlv lmklarpavl ddfvstidlp 601  nygctipekt scsvygwgyt glinydgllr vahlyimgne kcsqhhrgkv tlneseicag 661  aekigsgpce gdyggplvce qhkmrmvlgv ivpgrgcaip nrpgifvrva yyakwihkii 721  ltykvpqs
```

HGF agents may comprise full length HGF (SEQ ID NO: 1). HGF agents may also comprise truncated HGF or certain domains of the full length peptide, e.g., fragments of the full length or parent protein, e.g., HGF. The term "fragment," as used herein, means a portion of a polypeptide or polynucleotide that is less than the entire polypeptide or polynucleotide. As used herein, a "functional fragment" of a reference protein, e.g., HGF, is a fragment of the polypeptide that is shorter than the full-length, immature, or mature polypeptide and has at least 25% (e.g., at least 30%, 40%, 50%, 60%, 70%, 80%, 90%, 95%, 98%, 99%, or even 100% or more) of the activity of full-length mature reference protein. For example, the activity to reduce corneal haze or scarring. Methods of establishing whether a fragment of HGF is functional/active are known in the art, e.g., as determined by the criteria described in Table 1. For example, fragments of at least 70% amino acid identity, preferably at least 80% amino acid identity, more preferably at least 90% identity, and most preferably 95% identity to the fragments described herein are also included within the scope of the invention described herein.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 2A-FIG. 2C show images and quantification of corneal injury at days 1, 3, 5 and 7 post injury, photographs of injured cornea (with or without fluorescein (green) staining) were captured using slit-lamp biomicroscopy.

FIG. 7A: At 7 days post injury, corneas were harvested from normal, albumin-treated and HGF-treated mice. Corneal cross sections were stained with the nuclear stain DAPI to visualize corneal epithelial cell layer using confocal microscope (400×). FIG. 7B: Bar chart showing the thickness (µm) of the epithelial cell layer in normal (white bar), control-injured and HGF-treated injured corneas (black bar). The values shown are the mean±SD (error bars); n=5 mice/group.

DETAILED DESCRIPTION OF THE INVENTION

The present invention provides compositions, methods and treatment for corneal haze and scarring. The method for the treatment and prevention of corneal haze and scarring in humans is carried out by therapeutic administration of HGF or a fragment or agonists thereof onto or into the cornea or in combination with either pharmaceutically suitable vehicle or another therapeutic agent. The HGF agent comprises HGF or an agent able to induce HGF-mediated signal transduction by HGF-receptor (HGFR or cMET), and may include, without limitation, a natural protein, recombinant protein or peptide and fusion or chimeric protein able to bind HGFR, and biologic or chemical small molecule agonist of HGFR.

Corneal Anatomy

Figure 1:
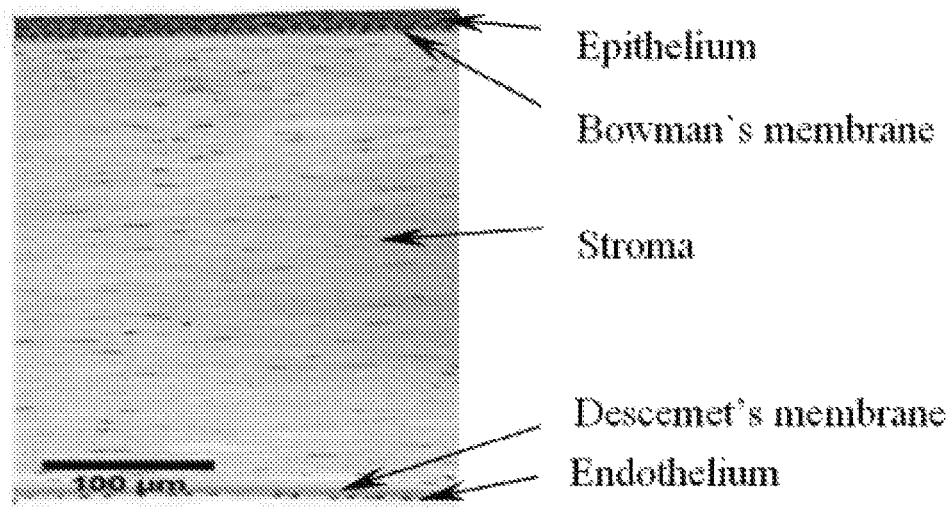
FIG. 1 is a diagram of corneal anatomy identifying the layers of the cornea.

The cornea is comprised of multiple layers with different thickness, cellular make-up and function. Layers of the cornea include the epithelium, bowman's membrane or layer, the stroma, Descemet's membrane or layer, and the endothelium. Each of the layers is illustrated in FIG. 1.

The epithelium is the layer of cells that cover the surface of the cornea. It is only about 5-6 cell layers thick and quickly regenerates when the cornea is injured. If the injury penetrates more deeply into the cornea, it may leave a scar. Scars leave opaque areas, causing the cornea to lose its clarity and luster.

Bowman's membrane lies just beneath the epithelium. Because this layer is very tough and difficult to penetrate, it protects the cornea from injury.

The stroma is the thickest layer and lies just beneath Bowman's membrane. It is composed of tiny collagen fibrils that run parallel to each other. This special formation of the collagen fibrils gives the cornea its clarity. HGF agents act at the stroma of the cornea to prevent and treat corneal haze or scarring. HGF agents inhibit expression of α-smooth muscle actin within the keratocytes of the corneal stroma to suppress keratocyte function and migration of inflammatory cells to corneal stroma that prevent development of corneal haze and scarring. These keratocytes do not exist in other corneal layers.

Corneal haze is not an epithelial or endothelial cell event. Corneal haze and scarring is a stromal condition, which primarily occurs due to the dysfunction of corneal stroma components, including excessive expression of actin and collagen fibers by keratocytes, and infiltration of inflammatory cells and differentiation of keratocytes into myofibroblasts. These cellular processes are distinct from corneal epithelial cell proliferation.

Descemet's membrane lies between the stroma and the endothelium.

The endothelium is just underneath Descemet's and is only one cell layer thick. This layer pumps water from the cornea, keeping it clear. If damaged or disease, these cells will not regenerate.

Previous methodologies utilized steroid therapy for the treatment of corneal haze and scarring. Table 3 below details the improvements of HGF therapy described herein compared with steroid therapy.

TABLE 3

|  | STEROIDS | HGF |
| --- | --- | --- |
| Therapeutic Effects | | |
| Anti-inflammatory | + | + |
| Anti-fibrotic | + | + |
| Cell Death | Decreases | Decreases |
| Corneal Epithelial cell proliferation and migration | Decreases | Increases |
| Adverse Effects | | |
| Action Spectrum | Non-selective | Targeted |
| Intraocular pressure | ++ | |
| Secondary Infection | + | − |

The mechanism of action of HGF is cell-specific in that it targets HGF-R expressing cells. Steroids are broad spectrum and non-selective in their action, which commonly lead to non-specific immunosuppression and secondary infection. As shown in Table 3, the risk of secondary infection is reduced using the compositions and methods described herein and cell proliferation is increased relative to treatment with steroids leading to reduced side effects and increased rates and further degree of healing and prevention.

Methods of Use

Provided here are methods of treating or preventing corneal haze or scarring by identifying a subject in need thereof; administering to the subject a HGFR-binding composition that includes at least one purified HGF agent. In embodiments, the administering comprises contacting the composition with corneal stroma of the subject. In embodiments, the identifying comprises calculating a grade scale of the subject's cornea transparency as described in Table 1.

The topical ophthalmic formulations are useful to treat corneal haze or scarring. Thus, the invention also provides methods for the treatment of corneal haze or scarring in a subject in need of such treatment by administering a composition described herein (e.g., an ophthalmic formulation of the present invention) directly to the eye or region of the eye of the subject. For example, administering step may comprise contacting the ophthalmic formulations described herein with corneal stroma or corneal stromal cells.

Pharmaceutical formulations comprising HGF agents fragments, or agonists thereof of the invention may be used for the treatment of corneal haze or scarring. For example, the pharmaceutical compositions are formulated for topical administration to the eye (e.g., subconjunctival administration; eye drops). Optionally, the pharmaceutical compositions may further comprise a tear substitute. Suitable tear substitutes may comprise glycerin, propylene glycol, HPMC (hydroxypropyl methylcellulose, hypromellose), Dextran 70, mineral oil, petrolatum, Carbopol 980, povidone, CMC (carboxyl methylcellulose sodium), PVA (polyvinyl alcohol) or other ingredients both active an inactive.

Also provided are methods for treating or preventing corneal haze or scarring in a subject in need thereof comprising administering to the eye surface of the subject a pharmaceutical composition comprising an effective amount of at least one (e.g., 1, 2, 3, 4, 5, 6, 7, 8, etc.) HGF agent(s). Optionally, the administration of HGF agent(s) to the eye of a subject in need of treatment or preventing corneal haze or scarring is also effective to mitigate or reduce one or more symptoms associated with a disease or condition on the corneal surface. An effective amount is an amount that reduces the haze/scarring score by at least one unit, e.g., the units shown in Table 1. For example, an effective amount reduces the score from a "+3" to a "+2". The subject is preferably a human, but may be another mammal, for example a dog, a cat, a rabbit, a mouse, a rat, or a non-human primate.

The formulations may contain an effective amount of HGF agent and optionally one or more additional active ingredients that are effective for the intended use. Particular dosages are also selected based on a number of factors including the age, sex, species and condition of the subject. Effective amounts can also be extrapolated from dose-response curves derived from in vitro test systems or from animal models. The term "effective amount" means an amount of HGF agent(s) that is sufficient to prevent, eliminate, or reduce corneal haze or scarring.

The effective amount is the amount sufficient for the treatment or prevention of corneal haze or scarring. "Treatment" in this context refers to reducing or ameliorating at least one symptom as a result of corneal haze or scarring. "Prevention" in this context refers to a reduction in the frequency of, or a delay in the onset of, symptoms associated with a disease or condition, relative to a subject who does not receive the composition. In some cases, the methods described herein inhibit differentiation of corneal fibroblasts for at least about 10%, 20%, 30%, 40%, 50%, 60%, 70%, 80%, 90% or more upon administration of a composition described herein compared to the level without administration of a composition described herein. In some cases, the methods described herein inhibit α-smooth muscle actin (αSMA) expression for at least about 10%, 20%, 30%, 40%, 50%, 60%, 70%, 80%, 90% or more upon administration of a composition described herein compared to the level without administration of a composition described herein. In some cases, the methods described herein increase stratification of corneal epithelial cells for at least 10%, 20%, 30%, 40%, 50%, 60%, 70%, 80%, 90% or more upon administration of a composition described herein compared to the level without administration of a composition described herein. In some cases, the methods described herein increase c-met expression for at least 10%, 20%, 30%, 40%, 50%, 60%, 70%, 80%, 90% or more upon administration of a composition described herein compared to the level without administration of a composition described herein. In some cases, the methods described herein restore the thickness of an injured cornea to about 50%, 60%, 70%, 80%, 90%, 95% or higher percentage of that of a normal (i.e., healthy) cornea thickness upon administration of a composition described herein. In some cases, the methods described herein inhibit trafficking of inflammatory leukocytes to an injured cornea for at least 10%, 20%, 30%, 40%, 50%, 60%, 70%, 80%, 90% or more upon administration of a composition described herein compared to the level without administration of a composition described herein.

The invention features methods of treating corneal haze or scarring in a subject comprising use of the formulations described above. For example, a method of treating corneal haze or scarring may comprise administering to the eye surface of the subject a pharmaceutical composition comprising an effective amount of at least one HGF agent and a tear substitute in a pharmaceutically acceptable carrier.

Ophthalmic Formulations

HGF agents may be formulated in combination with a suitable pharmaceutical carrier. Such formulations comprise a therapeutically effective amount of the HGF agent, and a pharmaceutically acceptable carrier (excipient). Such carriers include, but are not limited to, saline, buffered saline, dextrose, water, glycerol, ethanol, and combinations thereof. Formulation should suit the mode of administration, and is well within the skill of the art.

For example, the pharmaceutical compositions of the invention may comprise combinations of at least one (e.g., 1, 2, 3, 4, 5, 6, etc.) HGF agent. In embodiments, the pharmaceutical compositions are formulated for subconjunctival administration. For example, the pharmaceutical compositions are formulated for topical administration to the eye (e.g., subconjunctival administration; eye drops). The pharmaceutical compositions may further comprise a tear substitute.

The concentration of HGF agents are from about 0.001% to about 10.0% (w/v), e.g., about 0.001% to about 5%, about 0.001% to about 2.5%, about 0.001% to about 1%, about 0.001% to about 0.5%, about 0.005 to about 0.5%, about 0.005% to about 0.05%, about 0.01%. By way of example, the concentration of HGF agent is effective to restore corneal thickness to that of a normal corneal and/or to inhibit trafficking of inflammatory leukocytes to an injured cornea.

Preferably, the pharmaceutical compositions according to the present invention are formulated as solutions, suspensions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions.

Any of a variety of carriers may be used in the formulations of the present invention including water, mixtures of water and water-miscible solvents, such as C1- to C7-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. The concentration of the carrier is, typically, from 1 to 100000 times the concentration of the active ingredient. Additional ingredients that may be included in the formulation include tonicity enhancers, preservatives, solubilizers, non-toxic excipients, demulcents, sequestering agents, pH adjusting agents, co-solvents and viscosity building agents.

For the adjustment of the pH, preferably to a physiological pH, buffers may especially be useful. The pH of the present solutions should be maintained within the range of about 4.0 to 8.0 (e.g., about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8), more preferably about 4.0 to 6.0 (e.g., about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6), more preferably about 6.5 to 7.8 (e.g., about 6.5, 6.6, 6.7, 6.8, 6.9, 7, 7.1, 7.2, 7.3, 7.4, 7.5, 7.6, 7.7, 7.8). Suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred. Generally, buffers will be used in amounts ranging from about 0.05 to 10 percent by weight.

Tonicity is adjusted if needed typically by tonicity enhancing agents. Such agents may, for example be of ionic and/or non-ionic type. Examples of ionic tonicity enhancers are alkali metal or earth metal halides, such as, for example, $CaCl_2$, KBr, KCl, LiCl, NaI, NaBr or NaCl, $Na_2SO_4$ or boric acid. Non-ionic tonicity enhancing agents are, for example, urea, glycerol, sorbitol, mannitol, propylene glycol, or dextrose. The aqueous solutions of the present invention are typically adjusted with tonicity agents to approximate the osmotic pressure of normal lachrymal fluids which is equivalent to a 0.9%±0.1% solution of sodium chloride or a 2.5%±0.3% solution of glycerol. An osmolality of about 225 to 400 mOsm/kg is preferred, more preferably 280 to 320 mOsm.

The at least one HGF agent(s) may be administered by the use of or in the form of hydrogels, drug-eluting contact lenses, and nanosystems (liposomal systems, dendrimers, solid biodegradable nanoparticles, nanogels), and/or irrigating solutions.

Ophthalmic formulations, eye ointments, creams, salves, powders, solutions and the like, are also contemplated as being within the scope of this invention.

Eye Drops

The eye drop may be formulated with or without one or more tear substitutes. Also provided are pharmaceutical compositions comprising an effective amount of one or more (e.g., 1, 2, 3, 4, 5, 6, 7, 8, 9, etc.) HGF agent(s), and a tear substitute in a pharmaceutically acceptable carrier for the treatment of corneal haze or scarring. The HGF agents and tear substitute may act synergistically to provide a longer dwell time of the HGF agent on the cornea, thus increasing duration and efficacy of action.

A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as carbomer 934P, carbomer 941, carbomer 940 and carbomer 974P. Many such tear substitutes are commercially available, which include, but are not limited to cellulose esters such as Bion Tears®, Celluvisc®, Genteal®, OccuCoat®, Refresh®, Teargen II®, Tears Naturale@, Tears Natural II®, Tears Naturale Free®, and TheraTears®; and polyvinyl alcohols such as Akwa Tears®, HypoTears®, Moisture Eyes®, Murine Lubricating®, and Visine Tears®. Tear substitutes may also be comprised of paraffins, such as the commercially available Lacri-Lube® ointments. Other commercially available ointments that are used as tear substitutes include Lubrifresh PM®, Moisture Eyes PM® and Refresh PM®.

In one aspect, the tear substitute contains hydroxypropylmethylcellulose. The tear substitute is Genteal® lubricating eye drops. GenTeal® (CibaVision-Novartis) is a sterile lubricant eye drop containing hydroxypropyl methylcellulose 3 mg/g and preserved with sodium perborate.

The pharmaceutical compositions of the invention may comprise combinations of one or more HGF agent(s) and one or more tear substitutes.

Therapeutic Administration

The effective amount of the active agents in the formulation will depend on absorption, inactivation, and excretion rates of the drug as well as the delivery rate of the compound from the formulation. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of any compound of the present invention will vary depending on the symptoms, age and other physical characteristics of the patient, the nature and severity of the disorder to be treated or prevented, the degree of comfort desired, the route of administration, and the form of the supplement. Any of the subject formulations may be administered in a single dose or in divided doses. Dosages for the formulations of the present invention may be readily determined by techniques known to those of skill in the art or as taught herein.

An effective dose or amount, and any possible effects on the timing of administration of the formulation, may need to be identified for any particular formulation of the present invention. This may be accomplished by routine experiment as described herein. The effectiveness of any formulation and method of treatment or prevention may be assessed by administering the formulation and assessing the effect of the administration by measuring one or more indices associated with the efficacy of the active agent and with the degree of comfort to the patient, as described herein, and comparing the post-treatment values of these indices to the values of the same indices prior to treatment or by comparing the post-treatment values of these indices to the values of the same indices using a different formulation.

The precise time of administration and amount of any particular formulation that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

The combined use of several active agents formulated into the compositions of the present invention may reduce the required dosage for any individual component because the onset and duration of effect of the different components may be complimentary. In such combined therapy, the different active agents may be delivered together or separately, and simultaneously or at different times within the day.

Packaging

The formulations of the present invention may be packaged as either a single dose product or a multi-dose product. The single dose product is sterile prior to opening of the package and all of the composition in the package is intended to be consumed in a single application to one or both eyes of a patient. The use of an antimicrobial preservative to maintain the sterility of the composition after the package is opened is generally unnecessary.

Multi-dose products are also sterile prior to opening of the package. However, because the container for the composition may be opened many times before all of the composition in the container is consumed, the multi-dose products must have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP") and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing.")

Kits

This invention provides kits for the packaging and/or storage and/or use of the formulations described herein, as well as kits for the practice of the methods described herein. Thus, for example, kits may comprise one or more containers containing one or more ophthalmic solutions, tablets, or capsules of this invention. The kits can be designed to facilitate one or more aspects of shipping, use, and storage.

The kits may optionally include instructional materials containing directions (i.e., protocols) disclosing means of use of the formulations provided therein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g. CD ROM), and the like. Such media may include addresses to internet sites that provide such instructional materials.

Figure 2A:
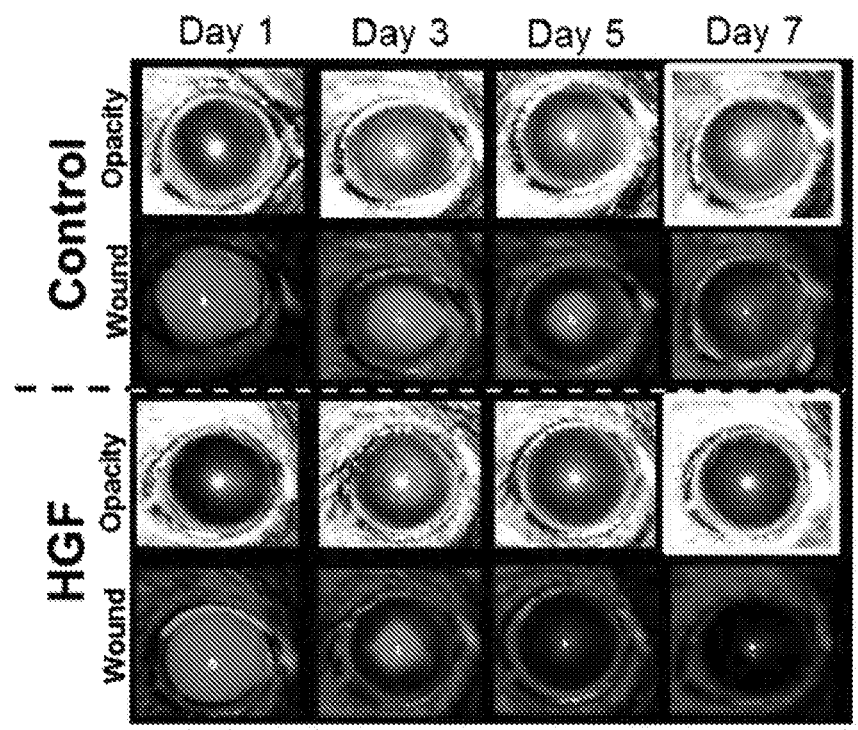
FIG. 2A is a photograph showing representative slit-lamp (bright-field and fluorescein) biomicroscopy images of injured cornea.
Figure 2B:
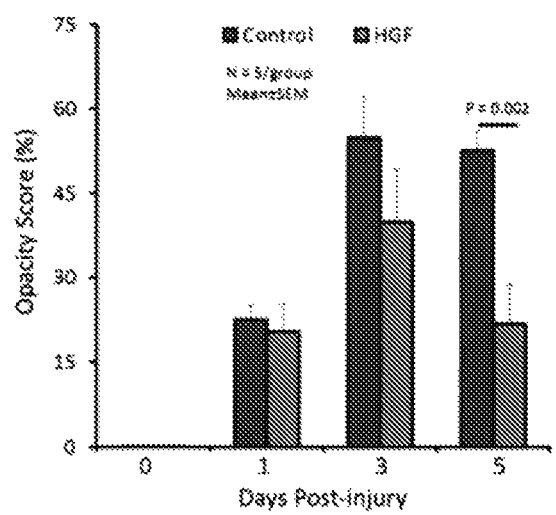
FIG. 2B is a bar graph displaying quantification of corneal opacity (haze/scarring) using Image J software shows a significant reduction in development of corneal opacity in HGF-treated mice compared to albumin-treated control group.
Figure 2C:
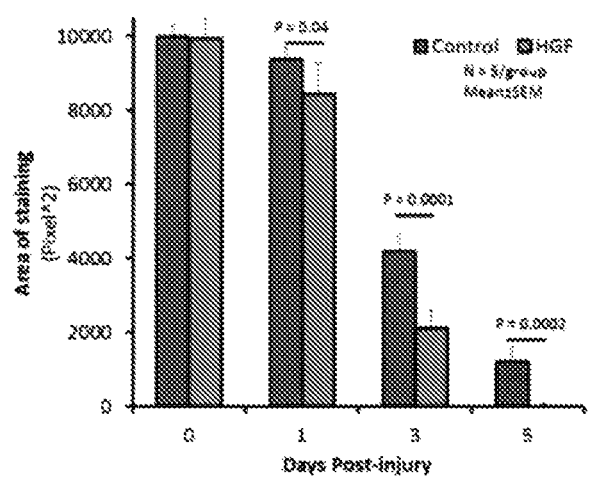
FIG. 2C is a bar graph showing quantification of fluorescein-stained area using Image J software shows significant reduction of fluorescein staining (i.e. injured area) in HGF-treated mice compared to control group. (N=5-6 mice/group).

Example 1: Topical HGF Inhibits Development of Corneal Haze and Scarring, and Promotes Wound Healing Corneal injury was induced by mechanical removal of the complete corneal epithelium using Algerbrush-II in C57131_6 mice. Complete removal of the corneal epithelium results in injury to the layers below including the corneal stroma. Under a dissecting microscope, the central area of the cornea was demarcated with a 3-mm trephine, and rotated gently to cut into the stroma. The circular area was traced with a sharp pair of surgical forceps, and then corneal epithelium and basement membrane, including the anterior portion of the stroma, were removed using a handheld ALGERBRUSH II™ (Alger Equipment Co., Tx). This type of wound leaves bare stroma with the epithelium and basement membrane removed, leading to a significant inflammatory response. Following injury, corneas will be flushed with sterile saline and subsequently HGF or control treatments were applied. Thereafter, murine recombinant HGF was topically applied (dose: 3 µl of 0.01% HGF in PBS per eye) to the injured eye twice daily up to 7 days post injury. A control group received a similar dosage of mouse serum albumin. At days 1, 3, 5 and 7 post injury, photographs of injured cornea (with or without fluorescein (green) staining) were captured using slit-lamp biomicroscopy. A smaller area of fluorescein (green) staining represents faster repair of corneal injury. FIG. 2A indicates reduced opacity and increased wound healing in the days following injury in treated animals relative to control. The decrease in opacity in treated animals is statistically significant at 5 days post injury (FIG. 2B). The decreased in wounded area indicated by the green staining is statistically decreased at 1, 3 and 5 days post injury (FIG. 2C).

Figure 3A:
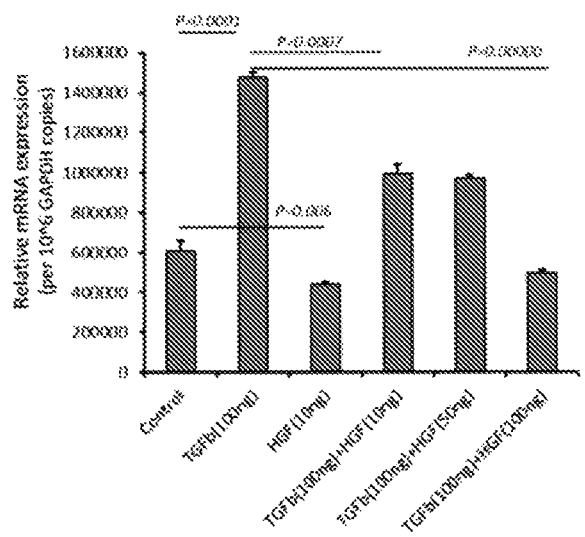
FIG. 3A is a bar graph and FIG. 3B is a series of photographs demonstrating that HGF inhibits expression of α-smooth muscle actin (αSMA: a factor that causes scarring) by corneal keratocytes. In vitro analysis of murine corneal keratocytes (MK/T1) shows that HGF significantly inhibits TGFp-induced expression of αSMA in keratocytes as measured by real time PCR (FIG. 3A) and immunohistochemistry (FIG. 3B).
Figure 3B:
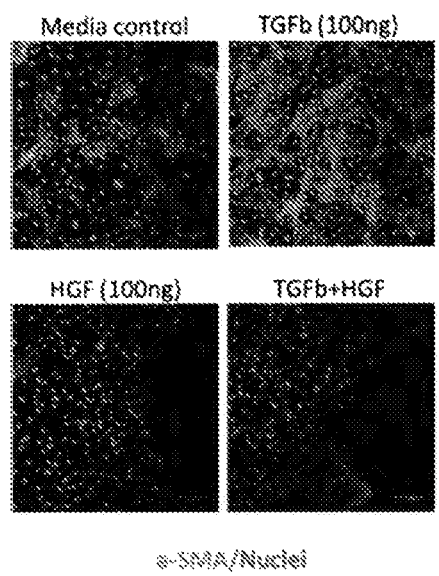

Example 2: HGF Inhibits Expression of α-Smooth Muscle Actin (αSMA: A Factor that Causes Scarring) by Corneal Keratocytes In vitro analysis of murine keratocytes (MK/T1) shows that HGF significantly inhibits TGFβ-induced expression of αSMA in keratocytes as measured by real time PCR (FIG. 3A) and immunohistochemistry (FIG. 3B). These keratocytes are present in the corneal stroma. HGF action in these cell types is indicative of HGF's functioning in the specialized cells of the corneal stroma, the corneal layer crucial for visual clarity.

Corneal haze and scarring in the stromal layer of the cornea can lead to visual degradation and blindness. Prevention, inhibition or reduction of scarring via inhibition of α-SMA in these tissues is effective to treat corneal haze and scarring and therefor aid improvement of vision.

Figure 4:
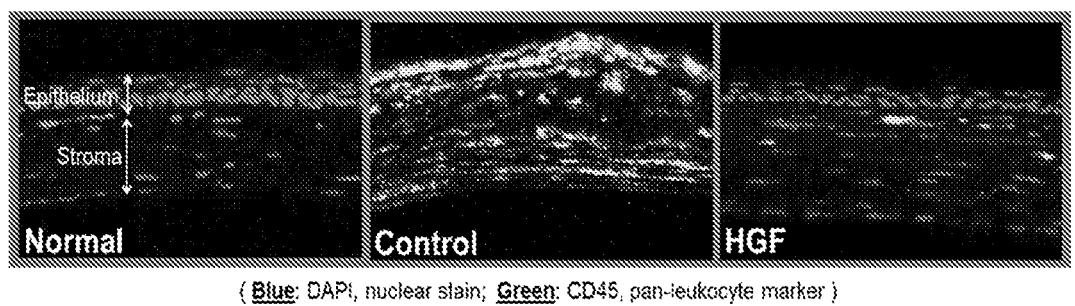
FIG. 4 is a confocal microscopy image showing immunostaining for pan leukocyte marker CD45 in corneas harvested 3-days post injury. Corneal injury was induced by mechanical removal of the complete corneal epithelium using ALGBERRUSH-II™ in C57BL6 mice. Thereafter, murine recombinant HGF was topically applied (dose: 3 µl of 0.01% HGF in PBS per eye) to the injured eye twice daily. A Control group received a similar dosage of mouse serum albumin. Blue coloration indicates DAPI staining of cell nuclei; green coloration indicates the presence of CD45, a pan-leukocyte marker.

Example 3: Topical HGF Treatment Inhibits Trafficking and Homing of Inflammatory Leukocytes to the Injured Corneas Corneal injury was induced by mechanical removal of the complete corneal epithelium using ALGERBRUSH-II™ in C57BL6 mice. Thereafter, murine recombinant HGF was topically applied (dose: 3 μl of 0.01% HGF in PBS per eye) to the injured eye twice daily. A control group received a similar dosage of mouse serum albumin. At day 3 post injury, corneas were harvested and immunostained for pan leukocyte marker CD45, and examined using confocal microscopy. (N=5 mice/group). Results are shown in FIG. 4: Blue coloration indicates DAPI staining of cell nuclei and green indicates staining for CD45, a pan-leukocyte marker.

Figure 5A:
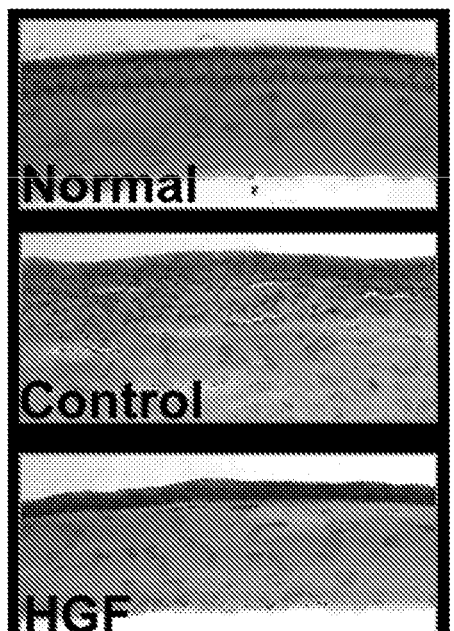
FIG. 5A is an image of representative micrographs showing tissue structure of normal, control injured and HGF-treated corneas.
Figure 5B:
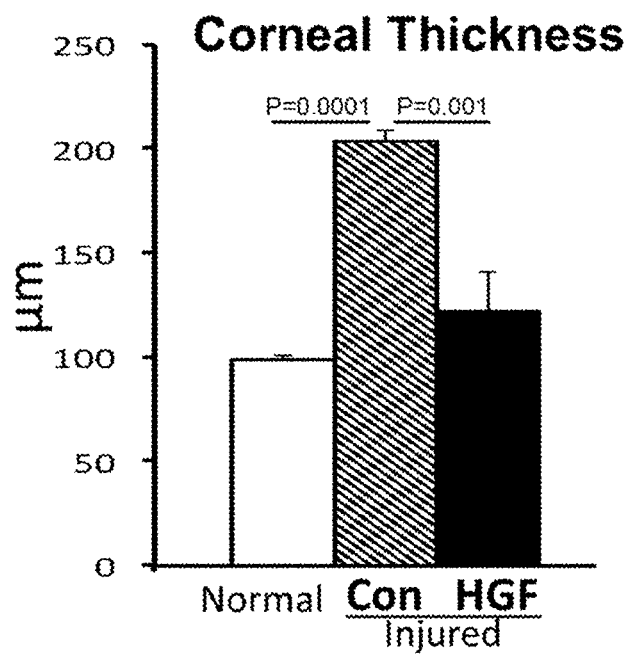
FIG. 5B is a bar graph of cumulative data showing HGF-treated corneas restore their thickness to a thickness similar to that of normal corneas. Injured control corneas show significant increase in the thickness as compared to normal and HGF-treated corneas. (N=5 mice/group).
Figure 6:
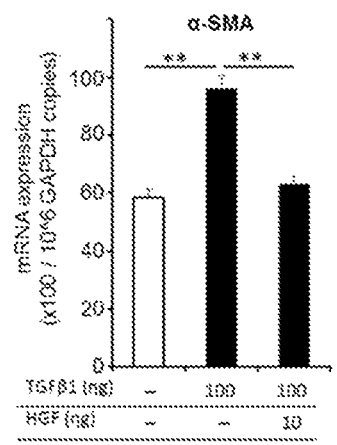
FIG. 6 is a bar graph showing that HGF inhibits differentiation of human corneal fibroblasts into myofibroblasts. Human corneal fibroblasts were stimulated with human recombinant TGFβ1 (100 ng/ml, Peprotech) in the presence or absence of rhHGF (10 ng/ml, R&D Systems) for 24 hrs. αSMA expression (normalized to internal control GAPDH) was evaluated using real-time PCR. The values shown are the mean±SD (error bars) from three independent experiments performed in triplicates; * p<0.02, ** p<0.001.

Example 4: Topical HGF Treatment Restores Corneal Tissue Structure and Thickness in Injury Corneal injury was induced by mechanical removal of the complete corneal epithelium using ALGERBRUSH-II™ in C57BL6 mice. Thereafter, murine recombinant HGF was topically applied (dose: 3 μl of 0.01% HGF in PBS per eye) to the injured eye twice daily. A control group received a similar dosage of mouse serum albumin. At day 7 post injury, corneas were harvested and cross sections were stained with hematoxylin and eosin (H&E). FIG. 5A shows representative micrographs showing tissue structure of normal, control injured and HGF-treated corneas. FIG. 5B presents cumulative data showing HGF-treated corneas restore their thickness similar to normal corneas. Injured control corneas show significant increase in the thickness as compared to normal and HGF-treated corneas. (N=5 mice/group).

Figure 7A:
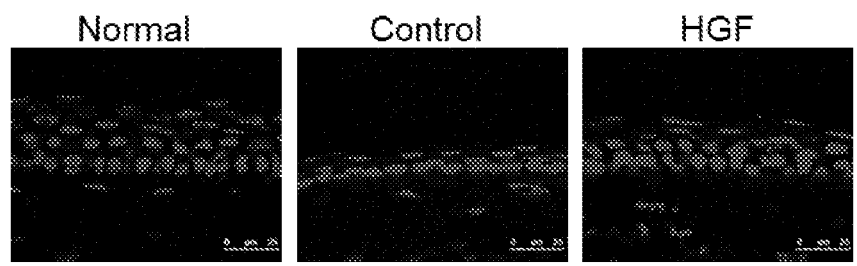
FIG. 7A is a series of images and FIG. 7B is a bar graph showing that HGF augments stratification of epithelial cells after corneal injury.
Figure 7B:
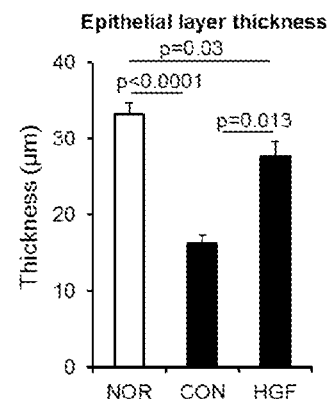

Example 5: HGF Treatment Augments Stratification of Epithelial Cells after Corneal Injury As shown in FIGS. 7A and 7B, HGF augments stratification of epithelial cells after corneal injury. At 7 days post injury, corneas were harvested from normal, albumin-treated and HGF-treated mice. Corneal cross sections were stained with the nuclear stain DAPI to visualize corneal epithelial cell layer using confocal microscope (400×) (FIG. 7A). Bar chart in FIG. 7B shows the thickness (μm) of the epithelial cell layer in normal (white bar), control-injured and HGF-treated injured corneas (black bar). The values shown are the mean±SD (error bars); n=5 mice/group.

Example 6: HGF Promotes HGF-R (c-Met) Expression

Figure 8:
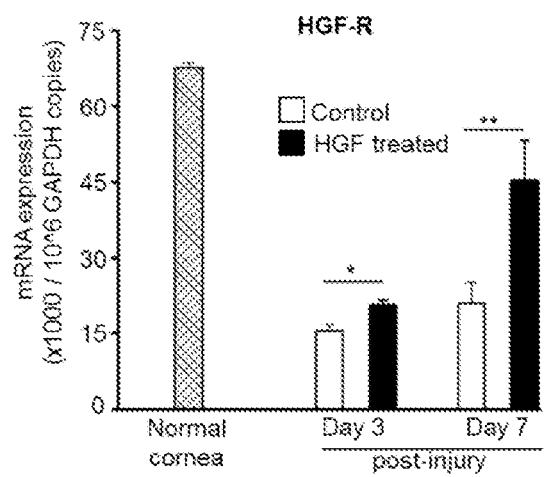
FIG. 8 is bar graph showing that HGF promotes HGF-R (c-met) expression in the cornea after injury. At 3 and 7 days post injury, corneas were harvested from normal (checked bar), mouse albumin-treated control injured (white bar) and HGF-treated (black bar) injured groups. Total RNA was isolated from harvested corneas. HGF-R mRNA expression was quantitated using real-time PCR GAPDH was used as a internal control. The values shown are the mean±SD and, each group consists of n=6 mice, *p<0.03, **p<0.01.

As shown in FIG. 8, HGF promotes HGF-R (c-met) expression in the cornea after injury. At 3 and 7 days post injury, corneas were harvested from normal (checked bar), mouse albumin-treated control injured (white bar) and HGF-treated (black bar) injured groups. Total RNA was isolated from harvested corneas. HGF-R mRNA expression was quantitated using real-time PCR. GAPDH was used as a internal control. The values shown are the mean±SD and, each group consists of n=6 mice, *$p<0.03$, **$p<0.01$.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating corneal haze or scarring comprising administering a composition comprising the purified hepatocyte growth factor (HGF) polypeptide of SEQ ID NO: 1 to a subject in need thereof, where the composition is topically administered to the cornea and the corneal haze or scarring is reduced in severity.

2. The method of claim 1, wherein the purified HGF agent is present in a concentration of 0.001% to 1% w/v.

3. The method of claim 1, wherein the HGF polypeptide is present in a concentration of about 0.005% to 0.05% w/v.

4. The method of claim 1, wherein the HGF polypeptide is present in a concentration of about 0.01% w/v.

5. The method of claim 1, wherein the composition is administered daily for 5 days after an injury to the cornea.

6. The method of claim 1, wherein the composition is administered daily for 3 days after an injury to the cornea.

7. The method of claim 1, wherein the composition is administered daily for 1 day after an injury to the cornea.

8. The method of claim 1, wherein the composition is formulated as an eye drop.

* * * * *